United States Patent [19]

Birbaum et al.

[11] Patent Number: 5,760,111
[45] Date of Patent: Jun. 2, 1998

[54] O-HYDROXYPHENYL-S-TRIAZINES

[75] Inventors: Jean-Luc Birbaum, Fribourg, Switzerland; Jürgen Kaschig, Freiburg; Dieter Reinehr, Kandern, both of Germany; Manfred Rembold, Pfeffingen, Switzerland; André Schmitter, Hegenheim, France; Helmut Luther, Grenzach-Wyhlen, Germany; Bernd Herzog, Bad Säckingen, Germany; Dietmar Hüglin, Freiburg, Germany

[73] Assignee: Ciba Specialty Chemicals Corporation, Tarrytown, N.Y.

[21] Appl. No.: 715,056

[22] Filed: Sep. 17, 1996

Related U.S. Application Data

[62] Division of Ser. No. 340,952, Nov. 17, 1994, Pat. No. 5,591,850.

[30] Foreign Application Priority Data

Nov. 23, 1993 [CH] Switzerland .................. 3488/93

[51] Int. Cl.[6] .................................................. C08K 5/3495
[52] U.S. Cl. .................................. 524/100; 529/91
[58] Field of Search ............................. 524/91, 100

[56] References Cited

U.S. PATENT DOCUMENTS

| 3,118,887 | 1/1964 | Hardy et al. ............ 260/248 |
| 3,268,474 | 8/1966 | Hardy et al. ............ 260/458 |

FOREIGN PATENT DOCUMENTS

| 0434608 | 6/1991 | European Pat. Off. . |
| 0444323 | 9/1991 | European Pat. Off. . |
| 1469811 | 2/1969 | Germany . |
| 0480090 | 12/1969 | Switzerland . |

*Primary Examiner*—Kriellion S. Morgan
*Attorney, Agent, or Firm*—Luther A. R. Hall; David R. Crichton; Michele Kovaleski

[57] ABSTRACT o-Hydroxyphenyl-s-triazines are described which contain at least two alkoxyphenyl substituents. They have the formula (1). The compounds according to the invention are suitable as stabilizers for textile fiber materials, in particular polyester fiber materials, and for organic polymers. Furthermore, they are suitable for use as sunscreens in cosmetic preparations.

5 Claims, No Drawings

O-HYDROXYPHENYL-S-TRIAZINES

This is a divisional of application No. 08/340,952 filed Nov. 17, 1994, now U.S. Pat. No. 5,591,850.

The present invention relates to o-hydroxyphenyl-s-triazines containing at least two alkoxyphenyl substituents, to processes for preparing these compounds, to the use for the photochemical and thermal stabilization of dyed and undyed polyester fibre materials, to the use of these compounds as stabilizers for organic polymers, to the polymer stabilized by these compounds, and to the use of these compounds as cosmetics.

The novel o-hydroxyphenyl-s-triazines have the formula

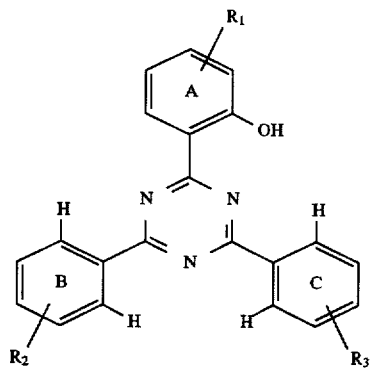 (1)

in which $R_1$ is hydrogen, hydroxyl, halogen, $C_1$–$C_{15}$alkyl, $C_1$–$C_{15}$alkoxy or a radical of the formula

 (1a)

$R_2$ and $R_3$ are each independently of the other hydrogen or $C_1$–$C_{15}$alkoxy. $R_4$ is $C_1$–$C_5$alkyl or $C_1$–$C_5$alkoxy-$C_1$–$C_5$alkyl, Q is an $C_1$–$C_4$alkylene radical, the rings A, B and C can contain further substituents and the compounds must contain at least two $C_1$–$C_{15}$alkoxy radicals.

$C_1$–$C_5$alkyl and $C_1$–$C_{15}$alkoxy are straight-chain or branched alkyl or alkoxy radicals, for example methyl, ethyl, n-propyl, isopropyl, n-butyl, sec-butyl, tert-butyl, amyl, isoamyl or tert-amyl, heptyl, octyl, isooctyl, nonyl, decyl, undecyl, dodecyl, tetradecyl or pentadecyl, or methoxy, ethoxy, propoxy, butoxy, pentyloxy, hexyloxy, heptyloxy, octyloxy, isooctyloxy, nonyloxy, undecyloxy, dodecyloxy, tetradecyloxy or pentadecyloxy. Preferably, the divalent radical Q contains 2 to 4 carbon atoms. Preferred divalent alkylene radicals are ethylene, ethylenepropylene or ethyleneisopropylene radicals.

Halogen is chlorine, bromine or iodine. Chlorine is preferred.

Preferably, suitable compounds of the formula (1) are those in which $R_1$ is hydrogen, hydroxyl, halogen, $C_1$–$C_{15}$alkyl, $C_1$–$C_{15}$alkoxy or $R_2$ and $R_3$ are each independently of the other hydrogen or $C_1$–$C_5$alkoxy, the rings A, B and C can contain further substituents and the compound must contain at least two $C_1$–$C_{15}$alkoxy radicals and in particular those compounds of the formula (1) in which the rings A and B are not further substituted or are substituted, independently of one another, by halogen, hydroxyl, $C_1$–$C_{15}$alkyl or $C_1$–$C_{15}$alkoxy.

Of particular interest are compounds of the formula (1) in which $R_2$ and $R_3$ are each independently of the other $C_1$–$C_5$alkoxy.

Of these, preference is given to those triazine compounds in which the substituents $R_2$ and $R_3$ are in the 3' or 4' position and in particular to those in which the substituents $R_2$ and $R_3$ are in the 4' position and very particular preference is given to those in which $R_2$ is hydrogen.

Particularly important compounds have the formula

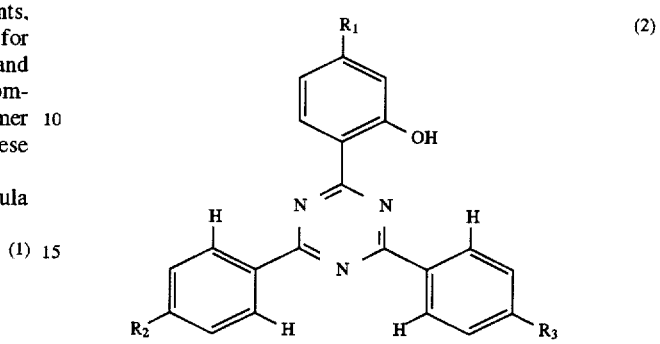 (2)

in which $R_1$ is hydrogen, hydroxyl, $C_1$–$C_{15}$alkyl, $C_1$–$C_{15}$alkoxy or a radical of the formula (1a), and $R_2$ and $R_3$ are each independently of the other hydrogen or $C_1$–$C_{15}$alkoxy.

Of the compounds of the formula (2), those are preferred in which $R_2$ and $R_3$ are methoxy or ethoxy, and in particular those in which $R_2$ is hydrogen and $R_3$ is methoxy or ethoxy, or those in which $R_1$ and $R_3$ are methoxy and $R_2$ is hydrogen.

Furthermore, preference is given to hydroxyphenyl-s-triazines of the formula (2) in which $R_1$, $R_2$ and $R_3$ are each independently of one another $C_5$–$C_{15}$alkoxy or to those compounds in which $R_1$ is a radical of the formula (1a) and $R_2$ and $R_3$ are $C_5$–$C_{15}$alkoxy.

Examples of compounds of the formula (1) include: 2-(2'-hydroxyphenyl)-4,6-bis(4-methoxyphenyl)-1,3,5-triazine 2-(2',4'-dihydroxyphenyl)-4,6-bis(4-methoxyphenyl)-1,3,5-triazine 2-(2'-hydroxy-3'-methylphenyl)-4,6-bis(4-methoxyphenyl)-1,3,5-triazine 2-(2',3'-dihydroxyphenyl)-4,6-bis(4-methoxyphenyl)-1,3,5-triazine 2-(2'-hydroxy-5'-chlorophenyl)-4,6-bis(4-methoxyphenyl)-1,3,5-triazine 2-(2'-hydroxy-4'-methoxyphenyl)-4,6-bis(4-methoxyphenyl)-1,3,5-triazine 2-(2',4'-dihydroxyphenyl)-4,6-bis(4-methoxyphenyl)-1,3,5-triazine 2-(2'-hydroxy-4'-hexyloxyphenyl)-4,6-bis(4-methoxyphenyl)-1,3,5-triazine 2-(2'-hydroxy-4'-hexyloxyphenyl)-4,6-bis(3-methoxyphenyl)-1,3,5-triazine 2-(2-hydroxy-4'-methoxyphenyl)-4-(4-methoxyphenyl)-6-phenyl-1,3,5-triazine 2-(2'-hydroxy-4'-[2-ethylhexyloxy]phenyl)-4,6-bis-(2-ethylhexyloxyphenyl)-1,3,5-triazine.

The compounds of the formulae (1) and (2) can be prepared by various methods.

For example, the compounds of the formulae (1) and (2) can be prepared in a one-step process by reacting a salicyl compound with a benzamidine compound. The preparation process comprises reacting a salicyl compound of the formula

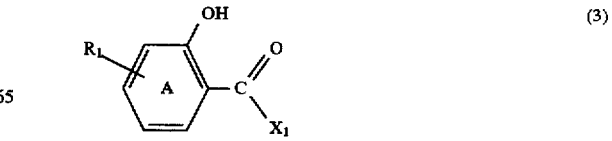 (3)

with a benzamidine compound of the formula

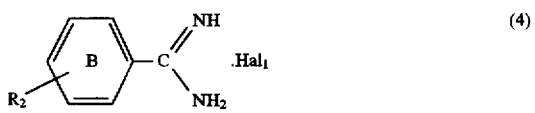

to give the triazine compound of the formula (1) where $R_1$, $R_2$, A and B are as defined in formula (1), $X_1$ is halogen or —$OR_4$, $R_4$ is $C_1$–$C_3$alkyl and $Hal_1$ is halogen.

The starting compounds of the formula (3) are substituted or unsubstituted salicylic esters or salicyl halides, for example methyl salicylate, ethyl salicylate or propyl salicylate or salicyl chloride or salicyl bromide, which may be substituted in the phenyl radical by further radicals in accordance with the meaning of A.

In the process according to the invention, the starting compounds of the formulae (3) and (4) can be used in different molar ratios.

Preferably, the molar ratios of the compound of the formula (3) to the compound of the formula (4) are 1:10 to 10:1.

In the case where the starting compound of the formula (3) is a salicyl halide ($X_1$=halogen), the molar ratio of the compound of the formula (3) to the compound of the formula (4) is preferably 1:3 to 1:2.

In the case where a salicylic ester ($X_1$=—$OR_4$) is used as the starting compound of the formula (3), the molar ratio of the compound of the formula (3) to the compound of the formula (4) is preferably 2:1 to 1:2.

Suitable benzamidine compounds of the formula (4) are benzamidine hydrobromide and, preferably, benzamidine hydrochloride, which may be further substituted in the phenyl radical in accordance with the meaning of B. These compounds are usually used as solid products having an active substance content of about 90–95%.

When the starting compound of the formula (3) used is a salicyl halide ($X_1$=halogen), at least the calculated amount of a base is usually added to neutralize the acid formed in the reaction. The bases used can be either organic or inorganic compounds, for example alkali metal hydroxide, in particular sodium hydroxide or potassium hydroxide solution; aqueous ammonia solution; ammonia gas; alkali metal carbonate, in particular sodium carbonate or potassium carbonate; sodium acetate; tertiary amines, such as pyridine or trialkylamines, in particular triethylamine, N,N-dimethylcyclohexylamine, N,N-dimethylaniline; alkali metal alkoxides, in particular sodium methoxide and potassium methoxide or potassium tert-butoxide.

The process according to the invention is usually carried out in such a manner that the salicylic and the benzamidine compounds are first introduced into an inert solvent.

Suitable inert solvents include aliphatic hydrocarbons and mixtures thereof, for example cyclohexane, or aromatic hydrocarbons, such as toluene, or dimethylacetamide or mixtures of these solvents.

When the starting compound of the formula (3) used is a salicyl halide ($X_1$=Hal), a further, usually polar, solvent, for example acetonitrile or dioxane, can be added.

The reaction time for the process according to the invention is in general 2 to 30 hours. Depending upon whether the starting compound of the formula (3) used is a salicyl halide ($X_1$=Hal) or a salicylic ester ($X_1$=—$OR_4$), the reaction times may vary. When using a salicylic ester, the reaction time is preferably 4 to 30 hours, in particular 18 to 22 hours. When using a salicyl halide, the reaction times are somewhat shorter. They are preferably 2 to 20 hours, in particular 4 to 8 hours.

The reactions are usually slightly exothermic. However, the reaction temperature should not exceed 95° C. since higher temperatures may lead to the formation of by-products, for example nitrile compounds from benzamidines. In practice, the reaction is carried out in a temperature range from 60° to 95° C., preferably 80° to 95° C.

Furthermore, the compounds of the formula (1) according to the invention can be prepared by dehydrogenating a dihydrotriazine compound of the formula

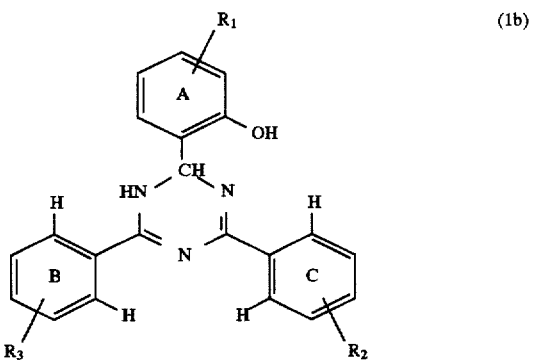

In this formula, $R_1$, $R_2$, $R_3$, A, B and C are as defined in formula (1).

The dehydrogenating agent used is usually chloranil. Dehydrogenation of dihydrotriazine compounds with chloranil to give 1,3,5-triazines is known, for example, from Khim. Geteritsikl. Soedin. (2), pp. 350–353 (1969).

The starting compounds of the formula (1b) are prepared in a manner known per se by reacting 2 mol of a suitable benzamidine hydrohalide compound with one mol of a suitable α-hydroxybenzaldehyde compound.

Another way of preparing the triazine compounds of the formula (1) is to react a monochlorotriazine compound of the formula

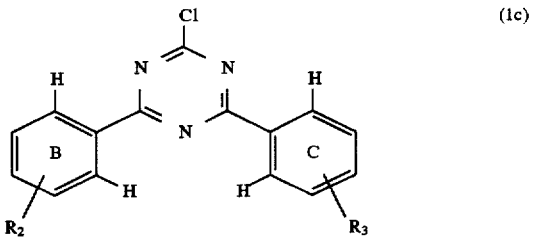

with an α-hydroxyphenyl compound of the formula

in the presence of a Lewis acid, in particular aluminium chloride.

In these formulae, $R_1$, $R_2$, $R_3$, A, B and C are as defined in formula (1). This reaction is known, for example, from J. Am. Chem. Soc. 73(7) (1951).

The starting compounds of the formula (1c) can be prepared in a manner known per se, for example by reacting cyanuric chloride with a corresponding phenylmagnesium bromide compound in a Grignard reaction. This reaction is known, for example, from Hirt et al., Helv. Chim. Acta, 33, 1368 (1950).

Furthermore, the triazine compounds according to the invention can be prepared by reacting an arenooxazinone compound of the formula

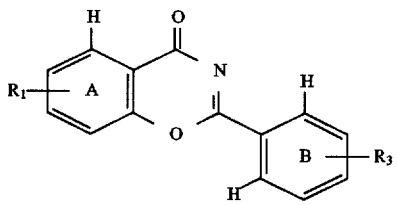

with a benzamidine compound of the formula (4). In these formulae, $R_1$, $R_2$, $R_3$, $Hal_1$, A, B and C are as defined.

The arenooxazinone compounds of the formula (6) and the preparation of these compounds are known, for example, from GB-B-1 155 506.

The compounds of the formula (1) are suitable for use as UV stabilizers, i.e. for protecting organic materials which are sensitive to ultraviolet light, in particular textile fibre materials, against the damaging effect of ultraviolet radiation.

Accordingly, the invention also provides a process for dyeing or printing polyester fibre materials and for the photochemical and thermal stabilization of these materials. The process comprises treating the fibre material by adding a compound of the formula (1) to the aqueous dyeing liquor or printing paste.

The triazine compounds of the formula (1) according to the invention are used in an amount of 0.01 to 10% by weight, preferably 0.1 to 5% by weight, relative to the weight of the fibre material.

The triazine compounds of the formula (1) are sparingly water-soluble and are therefore applied in dispersed form. To this end, they are milled together with a suitable dispersant to a particle size of about 1–2 μm using, for example, a quartz ball mill or a high-speed stirrer.

Examples of suitable dispersants for the compounds of the formula (1) are:

acidic esters or salts thereof of alkylene oxide adducts, for example acidic esters or salts thereof, of a polyaddition product of 4 to 40 mol of ethylene oxide with 1 mol of a phenol; or phosphoric esters of addition products of 6 to 30 mol of ethylene oxide with 1 mol of 4-nonylphenol, 1 mol of dinonylphenol or, in particular, with 1 mol of compounds prepared by addition reaction of 1 to 3 mol of substituted or unsubstituted styrenes with 1 mol of phenol, polystyrenesulfonates, fatty acid taurides, alkylated mono- or disulfonatodiphenyl oxides, sulfonates of polycarboxylic esters, addition products of 1 to 60, preferably 2 to 30, mol of ethylene oxide and/or propylene oxide with fatty amines, fatty amides, fatty acids or fatty alcohols each having 8 to 22 carbon atoms or with tri- to hexahydric alkanols having 3 to 6 carbon atoms, which addition products have been converted into an acidic ester by reaction with an organic dicarboxylic acid or an inorganic polybasic acid, lignosulfonates and, very particularly, formaldehyde condensation products, for example condensation products of lignosulfonates and/or phenol with formaldehyde, condensation products of formaldehyde with aromatic sulfonic acids, such as condensation products of ditolyl ether sulfonates with formaldehyde, condensation products of naphthalenesulfonic acid and/or naphthol- or naphthylamine sulfonic acids with formaldehyde, condensation products of phenolsulfonic acids and/or sulfonated dihydroxydiphenyl sulfone and phenols or cresols with formaldehyde and/or urea and condensation products of disulfodiphenyl oxide derivatives with formaldehyde.

Suitable dyes are disperse dyes which are only sparingly soluble in water. Accordingly, for the most part, they are present in the dyeing liquor in the form of a fine dispersion. They may belong to different classes of dyes, for example to acridone, azo, anthraquinone, coumarin, methine, perinone, naphthoquinoneimine, quinophthalone, styrene or nitro dyes. According to the invention, mixtures of disperse dyes can also be used.

Polyester fibre material which can be dyed or printed and treated with the triazine compounds mentioned is understood as meaning, for example, cellulose ester fibres, for example cellulose (secondary) acetate fibres and cellulose triacetate fibres and in particular linear polyester fibres which, if desired, may also be acid-modified and are obtained, for example, by condensing terephthalic acid with ethylene glycol or isophthalic acid or terephthalic acid with 1,4-bis(hydroxymethyl)cyclohexane, and fibres made of copolymers of terephthalic and isophthalic acid with ethylene glycol. The linear polyester fibre material used almost exclusively up to now in the textile industry consists of terephthalic acid and ethylene glycol.

The fibre materials can also be used as blend fabrics consisting of blends with each other or with other fibres, for example polyacrylonitrile/polyester, polyamide/polyester, polyester/cotton, polyester/viscose and polyester/wool blends, and can be dyed and also printed batchwise or continuously using known methods.

The textile material can be present in different make-up forms, preferably as piece goods, such as knitted fabrics or woven fabrics, or else as yarn on cheeses, warp beams and the like.

Furthermore, textile fabrics in the outerwear garment sector which are transparent are particularly suitable for the process according to the invention. When treated by the process according to the invention, such textiles are capable of protecting the skin tissue underneath the transparent outerwear fabric against the damaging effect of UV radiation.

Dyeing is carried out from an aqueous liquor by a continuous or batchwise method. In the batchwise method, the liquor ratio can be selected within a wide range, for example 4:1 to 100:1, preferably 6:1 to 50:1. The temperature at which dyeing is carried out is at least 50° C. and is usually not higher than 140° C. The preferred temperature range is from 80° to 135° C.

In the continuous dyeing method, the dyeing liquors, which, if desired, may contain, apart from the dyes, further auxiliaries, the dyeing liquors are applied to the piece material by, for example, padding or face padding and the dyes are fixed by thermofixing or HT steaming processes, preferably at 190° to 230° C. for 30 seconds to 3 minutes.

Linear polyester fibres and polyester blend fibres are preferably dyed by the so-called high-temperature method in closed and pressure-resistant apparatuses at temperatures of greater than 100° C., preferably between 110° and 135° C. and, if desired, under pressure. Examples of suitable closed vessels are circulation apparatuses, such as package-dyeing or beam-dyeing machines, winch backs, jet- or drum-dyeing machines, muff-dyeing machines, paddles or jiggers.

Cellulose (secondary) acetate fibres are preferably dyed at temperatures of 80°–85° C.

The UV stabilizers according to the invention can be used in the dye application before or after dyeing or else, which is preferred, by treating the fibre material simultaneously with the UV stabilizer and the dye in the dyeing bath.

The dyeing liquors can also contain further additives, for example dyeing assistants, dispersing agents, carriers, wool-protecting agents and wetting agents and also antifoams.

Furthermore, the dyeing baths can contain mineral acids, for example sulfuric acid or phosphoric acid, or, advantageously, organic acids, for example aliphatic carboxylic acids, such as formic acid, acetic acid, oxalic acid or citric acid, and/or salts, such as ammonium acetate, ammonium sulfate or sodium acetate. The acids are designed in particular for adjusting the pH of the liquors used according to the invention, which is preferably between 4 and 5.

Preferably, the fibre material is first pretreated in the bath which contains the dye, the UV stabilizer and any further additives and adjusted to a pH of 4.5 to 5.5 at 40° to 80° C. for 5 minutes, the temperature is then raised to 125° to 130° C. over a period of 10 to 20 minutes, and the treatment is continued at this temperature for 15 to 90 minutes, preferably 30 minutes.

The dyeings are finished by cooling the dyeing liquor to 50° to 80° C., rinsing the dyeings with water and, if desired, by reduction-clearing them in the usual manner in alkaline medium. The dyeings are then again rinsed and dried. When vat dyes are used for the cellulose portion, the material is first treated with hydrosulfite in the usual manner at a pH of 6 to 12.5 and then with an oxidizing agent and finally rinsed with water.

To produce prints, the triazine compounds according to the invention are admixed to the printing pastes in the form of their aqueous dispersions.

The printing paste contains the corresponding triazine compound in amounts of 0.1 to 10%, preferably 0.1 to 5%, relative to the weight of the printing paste.

The amount of dye added to the printing pastes depends on the desired shade. In general, amounts of 0.01 to 15, preferably 0.02 to 10, per cent by weight, relative to the textile material used, have proven to be advantageous.

The printing pastes advantageously contain, apart from the dyes and the aqueous UV stabilizer dispersion, acid-resistant thickeners, preferably those of natural origin, such as carob bean flour derivatives, in particular sodium alginate by itself or in a mixture with modified cellulose, in particular with, preferably, 20 to 25 per cent by weight of carboxymethylcellulose. In addition, the printing pastes can also contain acid donors, such as butyrolactone or sodium hydrogen phosphate, preservatives, sequestering agents, emulsifiers, water-insoluble solvents, oxidizing agents or deaerators.

Suitable preservatives are in particular formaldehyde-releasing agents, for example paraformaldehyde or trioxane, in particular about 30 to 40 per cent by weight aqueous formaldehyde solution; examples of suitable sequestering agents are sodium nitrilotriacetate, sodium ethylenediaminetetraacetate, in particular sodium polymetaphosphate, in particular sodium hexametaphosphate; suitable emulsifiers are in particular alkylene oxide adducts with a fatty alcohol, in particular an oleyl alcohol adduct with ethylene oxide; suitable water-insoluble solvents are high-boiling saturated hydrocarbons, in particular paraffins having a boiling range from about 160° to 210° C. (white spirit); examples of suitable oxidizing agents are aromatic nitro compounds, in particular aromatic mono- or dinitrocarboxylic acids or mono- or dinitrosulfonic acids which, if desired, may be present as an alkylene oxide adduct, in particular nitrobenzenesulfonic acid; and examples of suitable deaerators are high-boiling solvents, in particular turpentine oils, higher alcohols, preferably $C_8$–$C_{10}$ alcohols, terpene alcohols or deaerators based on mineral and/or silicone oils, in particular commercial formulations comprising about 15 to 25 per cent by weight of a mineral oil/silicone oil mixture and about 75 to 85 per cent by weight of a $C_8$ alcohol, for example 2-ethyl-n-hexanol.

When printing fibre materials, the printing paste is directly applied to the entire surface or part thereof of the fibre material, for which advantageously printing machines of customary design, for example intaglio printing, rotary screen printing and flat screen printing machines, are used.

After printing, the fibre material is dried at temperatures of up to 150° C., preferably at 80° to 120° C.

Fixing is then carried out by subjecting the material to a heat treatment at temperatures of, preferably, 100° to 220° C. The heat treatment is usually carried out with superheated steam under pressure.

Depending on the temperature, fixing may be carried out for 20 seconds to 10 minutes, preferably 4 to 8 minutes.

The prints are likewise finished in the usual manner by rinsing them with water, which, if desired, can be followed by an additional reduction-clearing in alkaline medium using, for example, sodium dithionite. In the latter case, the prints are again rinsed, hydroextracted and dried.

The process according to the invention makes it possible to obtain polyester dyeings and prints of high light fastness and sublimation fastness. In the process according to the invention no selective pre- or aftertreatment of the fibre material is necessary.

The compounds of the formula (1) can advantageously be used as stabilizers for organic polymers to protect them from being damaged by air, oxygen and heat. Accordingly, the invention also provides a process for stabilizing organic polymers to protect them from being damaged by light, oxygen and heat, which comprises admixing at least one compound of the formula (1) to these materials. Examples of such polymers to be stabilized are:

1. Polymers of monoolefins and diolefins, for example polypropylene, polyisobutylene, polybut-1-ene, poly-4-methylpent-1-ene, polyisoprene or polybutadiene and polymers of cycloolefins, for example of cyclopentene or norbornene; furthermore polyethylene (which, if desired, can be crosslinked), for example high-density polyethylene (HDPE), low-density polyethylene (LDPE), linear low-density polyethylene (LLDPE), branched low-density polyethylene (BLDPE).

Polyolefins, i.e. polymers of monoolefins such as are mentioned by way of example in the above paragraph, in particular polyethylene and polypropylene, can be prepared by various methods, in particular by the following methods:

a) by means of free radicals (usually at high pressure and high temperature).

b) by means of a catalyst, the catalyst usually containing one or more metals from groups IVb, Vb, VIb or VIII. These metals usually comprise one or more ligands, such as oxides, halides, alcoholates, esters, ethers, amines, alkyls, alkenyls and/or aryls which can be either π- or σ-coordinated. These metal complexes can be free or can be fixed on a support, for example on activated magnesium chloride, titanium(III) chloride, alumina or silica. These catalysts can be soluble or insoluble in the polymerization medium. The catalysts can be active as such in the polymerization, or further activators can be used, for example metal alkyls, metal hydrides, metal alkyl halides, metal alkyl oxides or metal alkyl oxanes where the metals are elements from groups Ia, Ia and/or IIIa. The activators can be modified, for example, by further ester, ether, amine or silyl ether groups. These catalyst systems are usually designated as Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low-density polyethylene (LLDPE) and mixtures thereof with low-density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and copolymers thereof with carbon monoxide, or ethylene/acrylic acid copolymers and salts thereof (ionomers), and terpolymers of ethylene with propylene and a diene, such as hexadiene, dicyclopentadiene or ethylidenenorbornene; furthermore mixtures of such copolymers with one another and with the polymers mentioned under 1), for example polypropylene/ethylene-propylene copolymers, LDPE/ethylene-vinyl acetate copolymers, LDPE/ethylene acrylic acid copolymers, LLDPE/ethylene-vinyl acetate copolymers, LLDPE/ethylene-acrylic acid copolymers and polyalkylene/carbon monoxide copolymers of alternating or random structure and mixtures thereof with other polymers, for example polyamides.

4. Hydrocarbon resins (for example $C_5$–$C_9$), including hydrogenated modifications thereof (for example tackifier resins), and mixtures of polyalkylenes and starch.

5. Polystyrene, poly(p-methylstyrene), poly($\alpha$-methylstyrene).

6. Copolymers of styrene or $\alpha$-methylstyrene with dienes or acrylic derivatives, for example styrene/butadiene, styrene/acrylonitrile, styrene/alkyl methacrylate, styrene/butadiene/alkyl acrylate and methacrylate, styrene/maleic anhydride, styrene/acrylonitrile/methyl acrylate; high impact strength mixtures of styrene copolymers with another polymer, for example a polyacrylate, a diene polymer or an ethylene/propylene/diene terpolymer; and block copolymers of styrene, for example styrene/butadiene/styrene, styrene/isoprene/styrene, styrene/ethylene-butylene/styrene or styrene/ethylene-propylene/styrene.

7. Graft copolymers of styrene or $\alpha$-methylstyrene, for example styrene on polybutadiene, styrene on polybutadiene/styrene or polybutadiene/acrylonitrile copolymers, styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene, styrene and alkyl acrylates or alkyl methacrylates on polybutadiene, styrene and acrylonitrile on ethylene/propylene/diene terpolymers, styrene and acrylonitrile on polyalkyl acrylates or polyalkyl methacrylates, styrene and acrylonitrile on acrylate/butadiene copolymers, and mixtures with the copolymers mentioned under 6), such as are known, for example, as so-called ABS, MBS, ASA or AES polymers.

8. Halogen-containing polymers, for example polychloroprene, chlorinated rubber, chlorinated or chlorosulfonated polyethylene, copolymers of ethylene and chlorinated ethylene, epichlorohydrin homo- and copolymers, in particular polymers of halogen-containing vinyl compounds, for example polyvinyl chloride, polyvinylidene chloride, polyvinyl fluoride, polyvinylidene fluoride; and copolymers thereof, such as vinyl chloride/vinylidene chloride, vinyl chloride/vinyl acetate or vinylidene chloride/vinyl acetate.

9. Polymers which are derived from $\alpha,\beta$-unsaturated acids and derivatives thereof, such as polyacrylates and polymethacrylates, and polymethyl methacrylates, polyacrylamides and polyacrylonitriles modified with butyl acrylate for imparting impact strength.

10. Copolymers of the monomers mentioned under 9) with one another or with other unsaturated monomers, for example acrylonitrile/butadiene copolymers, acrylonitrile/alkyl acrylate copolymers, acrylonitrile/alkoxyalkyl acrylate copolymers, acrylonitrile/vinyl halide copolymers or acrylonitrile/alkyl methacrylate/butadiene terpolymers.

11. Polymers which are derived from unsaturated alcohols and amines or acyl derivatives or acetals thereof, such as polyvinyl alcohol, polyvinyl acetate, polyvinyl stearate, polyvinyl benzoate, polyvinyl maleate, polyvinyl butyral, polyallyl phthalate, polyallylmelamine; and copolymers thereof with olefins mentioned under item 1.

12. Homo- and copolymers of cyclic ethers, such as polyalkylene glycols, polyethylene oxide, polypropylene oxide or copolymers thereof with bisglycidyl ethers.

13. Polyacetals, such as polyoxymethylene, and those polyoxymethylenes containing comonomers, for example ethylene oxide; polyacetals which are modified by thermoplastic polyurethanes, acrylates or MBS.

14. Polyphenylene oxides and polyphenylene sulfides and mixtures thereof with styrene polymers or polyamides.

15. Polyurethanes which are derived on the one hand from polyethers, polyesters and polybutadienes containing terminal hydroxyl groups and on the other hand from aliphatic or aromatic polyisocyanates, and precursors thereof.

16. Polyamides and copolyamides which are derived from diamines and dicarboxylic acids and/or from aminocarboxylic acids or the corresponding lactams, such as nylon 4, nylon 6, nylon 6/6, 6/10, 6/9, 6/12, 4/6, 12/12, 11, nylon 12, aromatic polyamides starting from m-xylene, diamine and adipic acids; polyamides prepared from hexamethylenediamine and iso- and/or terephthalic acid and, if desired, an elastomer as modifier, for example poly-2,4,4-trimethylhexamethyleneterephthalamide or poly-m-phenyleneisophthalamide. Block copolymers of the above-mentioned polyamides with polyolefins, olefin copolymers, ionomers or chemically bonded or grafted elastomers; or with polyethers, for example with polyethylene glycol, polypropylene glycol or polytetramethylene glycol. Furthermore polyamides or copolyamides modified with EPDM or ABS; and polyamides condensed during processing (RIM-polyamide systems).

17. Polyureas, polyimides, polyamidoimides and polybenzimidazoles.

18. Polyesters which are derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate, polyhydroxybenzoates, and block polyether esters which are derived from polyethers having terminal hydroxyl groups; further polyesters modified with polycarbonates or MBS.

19. Polycarbonates and polyester carbonates.

20. Polysulfones, polyether sulfones and polyether ketones.

21. Crosslinked polymers which are derived on the one hand from aldehydes and on the other hand from phenols, urea or melamine, such as phenol/formaldehyde, urea/formaldehyde and melamine/formaldehyde resins.

22. Drying and non-drying alkyd resins.

23. Unsaturated polyester resins which are derived from copolyesters of saturated and unsaturated dicarboxylic acids with polyhydric alcohols, and vinyl compounds as crosslinking agents, and also halogen-containing modifications thereof of low flammability.

24. Crosslinkable acrylic resins which are derived from substituted acrylic esters, for example from epoxy acrylates, urethane acrylates or polyester acrylates.

25. Alkyd resins, polyester resins and acrylate resins which are crosslinked with melamine resins, urea resins, polyisocyanates or epoxy resins.

26. Crosslinked epoxy resins which are derived from polyepoxides, for example from bisglycidyl ethers or from cycloaliphatic diepoxides.

27. Natural polymers, such as cellulose, natural rubber, gelatin, and derivatives thereof which are chemically modified in a polymer-homologous manner, such as cellulose acetates, cellulose propionates and cellulose butyrates or cellulose ethers, such as methylcellulose; and rosin resins and their derivatives.

28. Mixtures (polyblends) of the polymers mentioned above, for example PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/nylon 6.6 and copolymers, PA/HDPE, PA/PP, PA/PPO.

Particular preference is given to the use of the compounds according to the invention as stabilizers in surface coatings of any type. This also means a process in accordance with the above description in which the organic polymer is a binder for a coating. The coatings can be pigmented or unpigmented coatings or metallic effect paints. They may contain an organic solvent or may be solvent-free or may be water-borne coatings.

The coatings can contain, as the binder, at least one of the polymers listed above. Examples of coatings containing specific binders are as follows:

1. Coatings based on cold- or hot-crosslinkable alkyd, acrylate, polyester, epoxy or melamine resins or mixtures of such resins, where appropriate with the addition of an acid curing catalyst; 2. Two-component polyurethane coatings based on hydroxyl-containing acrylate, polyester or polyether resins and aliphatic or aromatic polyisocyanates; 3. One-component polyurethane coatings based on blocked polyisocyanates which are unblocked during stoving,; 4. Two-component coatings based on (poly)ketimines and aliphatic or aromatic polyisocyanates; 5. Two-component coatings based on (poly)ketimines and an unsaturated acrylate resin or a polyacetoacetate resin or a methyl methylacrylamidoglycolate; 6. Two-component coatings based on carboxyl- or amino-containing polyacrylates and polyepoxides; 7. Two-component coatings based on anhydrido-containing acrylate resins and a polyhydroxy or polyamino component; 8. Two-component coatings based on (poly)oxazolidines and anhydrido-containing acrylate resins or unsaturated acrylate resins or aliphatic or aromatic polyisocyanates. 9. Two-component coatings based on unsaturated polyacrylates and polymalonates; 10. Thermoplastic polyacrylate coatings based on thermoplastic acrylate resins or separately crosslinking acrylate resins in combination with etherified melamine resins; 11. Coating systems based on siloxane-modified or fluorine-modified acrylate resins.

The coatings can also be radiation-curable coatings. In this case, the binder comprises monomeric or oligomeric compounds which contain ethylenic double bonds and are converted into a crosslinked high-molecular weight form by irradiation with actinic light or with electron beams. In most cases, the binder is a mixture of such compounds.

The coatings can be applied in a single coat or in two coats, the stabilizers according to the invention being preferably added to the unpigmented uppermost coat.

The coatings can be applied to the substrates (metal, plastic, wood, and the like) by customary methods, for example by brushing, spraying, pouring, dipping or by electrophoresis.

The amount of the stabilizer of the formula (1) added depends on the particular substrate and its intended use. In general, amounts of 0.01 to 5% by weight are sufficient, the amount used being preferably 0.05 to 3% by weight, relative to the polymer to be stabilized. According to the invention, polymers containing 0.01 to 5% by weight, in particular 0.05 to 3% by weight, of at least one compound of the formula (1) are therefore particularly suitable.

In certain cases, it may be advantageous to use two or more compounds of the formula (1). In addition, one or more further stabilizers and/or other additives may be included, for example the following types of compounds:

1. Antioxidants 1.1. Alkylated monophenols, for example, 2,6-di-tert-butyl-4-methylphenol, 2-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-($\alpha$-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alklthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl) adipate.

1.4. Hydroxylated thiodiphenyl ethers, for example 2,2'-thiobis(6-tert-butyl-4-methylphenol), 2,2'-thiobis(4-octylphenol), 4,4'-thiobis (6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-1-hydroxyphenyl) disulfide.

1.5. Alkylidenebisphenols, for example 2,2'-methylenebis (6-tert-butyl-4-methylphenol), 2,2'-methylenebis (6-tert-butyl-4-ethylphenol), 2,2'-methylenebis [4-methyl-6-($\alpha$-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis [6-($\alpha$,-methylbenzyl)-4-nonylphenol], 2,2'-methylenebis [6- ($\alpha$,$\alpha$-dimethylbenzyl)-4-nonylphenol], 4,4'-methylenebis (2,6-di-tert-butylphenol), 4,4'-methylenebis(6-tert-butyl-2-methylphenol), 1,1-bis(5-tertbutyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylthiobutane, ethylene glycol bis [3,3-bis(3'-tert-butyl-4'-hydroxyphenyl)butyrate], bis (3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl] terephthalate, 1,1-bis(3,5-dimethyl-2-hydroxyphenyl) butane, 2,2-bis-(3,5-di-tert-butyl-4-hydroxyphenyl)propane, 2,2-bis-(5-tert-butyl-4-hydroxy-2-methylphenyl)-4-n-dodecylthiobutane, 1,1,5,5-tetrakis (5-tert-butyl-4-hydroxy-2-methylphenyl)pentane.

1.6. O-, N- and S-benzyl compounds, for example 3,5,3',5'-tetra-tert-butyl-4,4'-dihydroxydibenzyl ether, octadecyl S-(4-hydroxy-3,5-dimethylbenzylthio) acetate, tris(3,5-di-tert-butyl-4-hydroxybenzyl)amine, bis(4-tert-butyl-3-hydroxy-2,6-dimethylbenzyl) dithioterephthalate, bis(3,5-di-tert-butyl-4-hydroxybenzyl)sulfide, isooctyl S-(3,5-di-tert-butyl-4-hydroxybenzylthio)acetate.

1.7. Hydroxybenzylated malonates, for example dioctadecyl 2,2-bis-(3,5-di-tert-butyl-2-hydroxybenzyl) malonate, dioctadecyl 2-(3-tert-butyl-4-hydroxy-5-methylbenzyl) malonate, didodecylthioethyl 2,2-bis-(3,5-di-tert-butyl-4-hydroxybenzyl) malonate, di [4-(1,1,3,3-tetramethylbutyl) phenyl] 2,2-bis(3,5-di-tert-butyl-4-hydroxybenzyl) malonate.

1.8. Hydroxybenzylaromatic compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.9. Triazine compounds, for example 2,4-bis(octylthio)-6-(3,5-di-tert-butyl-4-hydroxyanilino)-1,3,5-triazine, 2-octylthio-4,6-bis(3,5-di-tert-butyl-4-hydroxyanilino)-1,3,5-triazine, 2-octylthio-4,6-bis(3,5-di-tert-butyl-4-hydroxyphenoxy)-1,3,5-triazine, 2,4,6-tris(3,5-di-tert-butyl-4-hydroxyphenoxy)-1,3,5-triazine, 1,3,5-tris-(3,5-di-tert-butyl-4-hydroxybenzyl)isocyanurate, 1,3,5-tris(4-tert-butyl-3-hydroxy-2,6-dimethylbenzyl) isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.10. Benzylphosphonates, for example dimethyl 2,5-di-tert-butyl-4-hydroxybenzylphosphonate, diethyl 3,5-di-tert-butyl-4-hydroxybenzylphosphonate, dioctadecyl 3,5-di-tert-butyl-4-hydroxybenzylphosphonate, dioctadecyl 5-tert-butyl-4-hydroxy-3-methylbenzylphosphonate, the calcium salt of ethyl 3,5-di-tert-butyl-4-hydroxybenzylphosphonate.

1.11. Acylaminophenols, for example 4-hydroxylauranilide, 4-hydroxystearanilide, octyl N-(3,5-di-tert-butyl-4-hydroxyphenyl)carbamate.

1.12. Esters of β-(3,5-di-tert-butyl-4-hydroxyphenyl) propionic acid with mono- or polyhydric alcohols, e.g. with methanol, ethanol, octadecanol, 1,6-hexanediol, 1,9-nonanediol, ethylene glycol, 1,2-propanediol, neopentylglycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.13. Esters of β-(5-tert-butyl-4-hydroxy-3-methylphenyl) propionic acid with mono- or polyhydric alcohols, e.g. with methanol, ethanol, octadecanol, 1,6-hexanediol, 1,9-nonanediol, ethylene glycol, 1,2-propanediol, neopentylglycol, thiodiethylene glycol, diethylene glycol, triethylene glycol, pentaerythritol, tris(hydroxyethyl) isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(3,5-dicyclohexyl-4-hydroxyphenyl) proPionic acid with mono- or polyhydric alcohols, e.g. with methanol, ethanol, octadecanol, 1,6-hexanediol, 1,9-nonanediol, ethylene glycol, 1,2-propanediol, neopentylglycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of 3,5-di-tert-butyl-4-hydroxyphenyl acetic acid with mono- or polyhydric alcohols, e.g. with methanol, ethanol, octadecanol, 1,6-hexanediol, 1,9-nonanediol, ethylene glycol, 1,2-propanediol, neopentylglycol, thiodiethylene glycol, diethylene glycol, triethylene glycol, pentaerythritol, tris(hydroxyethyl) isocyanurate, N,N'-bis (hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Amides of β-(3,5-di-tert-butyl-4-hydroxyphenyl) propionic acid, e.g. N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine, N,N'-bis(3,5-di-tert-butyl-4-hydroxyphenylpropionyl)hydrazine.

2. UV absorbers and light stabilizers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl) benzotriazole, 2-(2'-hydroxy-4'-octoxyphenyl) benzotriazole, 2-(3',5'-di-tert-amyl-2'-hydroxyphenyl) benzotriazole, 2-(3',5'-bis (α,α-dimethylbenzyl)-2'-hydroxyphenyl)benzotriazole, mixture of 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)-phenyl)benzotriazole, 2-(3'-tert-butyl-2'-hydroxy-5'-(2-octyloxycarbonylethyl)-phenyl)benzotriazole, 2-(3'-tert-butyl-5'-[2-(2-ethylhexyloxy)carbonylethyl]-2∝-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl)phenyl) benzotriazole, 2,2'-methylenebis [4-(1,1,3,3-tetramethylbutyl)6-benzotriazol-2-ylphenol]; transesterification product of 2-[3'-tert-butyl-5'-(2-methoxycarbonylethyl)-2'-hydroxyphenyl]benzotriazole with polyethylene glycol 300; [R—$CH_2CH_2$—COO($CH_2$)$_3$]$_2$ where R=3'-tert-butyl-4'-hydroxy-5'-2H-benzotriazol-2-ylphenyl.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy, 2'-hydroxy-4,4'-dimethoxy derivative.

2.3. Esters of substituted or unsubstituted benzoic acids, for example 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl or isooctyl α-cyano-β,β-diphenylacrylate, methyl α-carbomethoxy cinnamate, methyl or butyl α-cyano-β-methyl-p-methoxycinnamate, methyl α-carbomethoxy-p-methoxy cinnamate, N-(β-carbomethoxy-β-cyanovinyl)-2-methylindoline.

2.5. Nickel compounds, for example nickel complexes of 2,2'-thiobis[4-(1,1,3,3-tetra-methylbutyl)phenol], such as the 1:1 or 1:2 complex, with or without additional ligands, such as n-butylamine, triethanolamine or N-cyclohexyldiethanolamine, nickel dibutyl dithiocarbamate, nickel salts of monoalkyl 4-hydroxy-3,5-di-tert-butylbenzyl-phosphonates, such as those of the methyl or ethyl ester, nickel complexes of ketoximes, such as those of 2-hydroxy-4-methylphenyl undecyl ketoxime, nickel complexes of 1-phenyl-4-lauroyl-5-hydroxypyrazole, with or without additional ligands.

2.6. Sterically hindered amines, for example bis(2,2,6,6-tetramethylpiperidyl) sebacate, bis(2,2,6,6-tetramethylpiperidyl) succinate, bis(1,2,2,6,6-pentamethylpiperidyl) sebacate, bis (1,2,2,6,6-pentamethylpiperidyl) 2-n-butyl-2-(3,5-di-tert-butyl-4-hydroxy-benzyl)malonate, condensation product of 1-hydroxyethyl-2,2,6,6-tetramethyl-4-hydroxy-piperidine with succinic acid, condensation product of N,N'-bis(2,2,6,6-tetramethyl-4-piperidyl)hexamethylenediamine with 4-tert-octylamino-2,6-dichloro-1,3,5-s-triazine, tris(2,2,6,6-tetramethyl-4-piperidyl)nitrilotriacetate, tetrakis-(2,2,6,6-tetramethyl-4-piperidyl) 1,2,3,4-butanetetracarboxylate, 1,1'-(1,2-ethanediyl) bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl) 2-n-butyl-2-(2-hydroxy-3,5-di-tert-butylbenzyl)malonate, 3-n-octyl-7,7,9,9-tetramethyl-1,3,8-triazaspiro-[4.5]decane-2,4-dione, bis(1-octyloxy-2,2,6,6-tetramethylpiperidyl) sebacate, bis(1-octyloxy-2,2,6,6-tetramethylpiperidyl) succinate, condensation product of N,N'-bis(2,2,6,6-tetramethyl-4-piperidyl) hexamethylenediamine with 4-morpholino-2,6-dichloro-1,3,5-triazine, condensation product of 2-chloro-4,6-di(4-n-butylamino-2,2,6,6-tetramethylpiperidyl)-1,3,5-triazine with 1,2-bis(3-aminopropylamino)ethane, condensation product of 2-chloro-4,6-di-(4-n-butylamino-1,2,2,6,6-pentamethylpiperidyl)-1,3,5-triazine with 1,2-bis(3-aminopropylamino)ethane, 8-acetyl-3-dodecyl-7,7,9,9-tetra-methyl-1,3,8-triazaspiro [4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)-pyrrolidine-2,5-dione.

2.7. Oxamides, for example 4,4'-dioctyloxyoxanilide, 2,2'-dioctyloxy-5,5'-di-tert-butyloxanilide, 2,2'-di-dodecyloxy-5,5'-di-tert-butyloxanilide, 2-ethoxy-2'-ethyloxanilide, N,N'-bis(3-dimethylaminopropyl)oxamide, 2-ethoxy-5-tert-butyl-2'-ethyloxanilide and its mixture with 2-ethoxy-2'-ethyl-5,4'-di-tert-butyloxanilide, mixtures of o- and p-methoxy- and of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethyl-phenyl)-1,3,5-triazine, 2-(2,4-dihydroxyphenyl)-4,6-bis(2,4-dimethylphenyl)-1,3,5-triazine, 2,4-bis (2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy- 4-dodecyloxyphenyl)-4,6-bis (2,4-dimethylphenyl)-1,3,5-triazine, 2-[2-hydroxy-4-(2-hydroxy-3-butyloxypropyloxy)phenyl]-4,6-bis(2,4-dimethylphenyl)-1,3,5-triazine, 2-[2-hydroxy-4-(2-hydroxy-3-octyloxypropyloxy)phenyl]-4,6-bis(2,4-dimethylphenyl)-1,3,5-triazine.

3. Metal deactivators, for example N,N'-diphenyloxamide, N-salicylal-N'-salicyloyl-hydrazine, N,N'-bis-(salicyloyl) hydrazine, N,N'-bis(3,5-di-tert-butyl-4-hydroxyphenylpropionyl)hydrazine, 3-salicyloylamino-1,2,4-triazole, oxalic bis(benzylidene hydrazide), oxanilide, isophthalic dihydrazide, sebacic bis(phenylhydrazide), adipic N,N'-bis (acetylhydrazide), oxalic N,N'-bis(salicyloylhydrazide), thiopropionic N,N'-bis (salicyloylhydrazide).

4. Further phosphites and phosphonites, for example triphenyl phosphite, diphenyl alkyl phosphite, phenyl dialkyl phosphite, tris(nonylphenyl) phosphite, trilauryl phosphite, tri-octadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl) pentaerythritol diphosphite, bis(isodecyloxy) pentaerythritol diphosphite, bis(2,4-di-tert-butyl-6-methylphenyl) pentaerythritol diphosphite, bis(2,4,6-tri-tert-butylphenyl) pentaerythritol diphosphite, tristearyl sorbitol triphosphite, tetrakis(2,4-di-tert-butylphenyl) 4,4'-biphenylenediphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl-12-methyldibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite.

5. Peroxide-destroying compounds, for example esters of β-thiodipropionic acid, for example the lauryl, stearyl, myristyl or tridecyl ester, mercaptobenzimidazole, the zinc salt of 2-mercaptobenzimidazole, zinc dibutyl dithiocarbamate, dioctadecyl disulfide, pentaerythritol tetrakis(β-dodecylthiopropionate).

6. Polyamide stabilizers, for example copper salts in combination with iodides and/or phosphorus compounds and divalent manganese salts.

7. Basic co-stabilizers, for example melamine, polyvinylpyrrolidone dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate, potassium palmitate, antimony pyrocatecholate or tin pyrocatecholate.

8. Nucleating agents, for example 4-tert-butylbenzoic acid, adipic acid, diphenyl acetic acid.

9. Fillers and reinforcing agents, for example calcium carbonate, silicate, glass fibres, asbestos, talc, kaolin, mica, barium sulfate, metal oxides and metal hydroxides, carbon black, graphite.

10. Other additives, for example plasticizers, lubricants, emulsifiers, pigments, fluorescent whiteners, flame retardants, antistatics, blowing agents.

11. Benzofuranones and indolinones, such as are described, for example, in U.S. Pat. No. 4,325,863 or U.S. Pat. No. 4,338,244.

Of particular importance are stabilized polymers which contain an additional amount of a light stabilizer from the class of sterically hindered amines and/or from the class of 2-(2'-hydroxyphenyl)benzotriazoles. Sterically hindered amines are understood as meaning in particular those compounds containing one or more groups of the formula

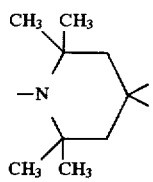

in the molecule, it being possible for these compounds to be monomeric, oligomeric or polymeric. Examples of such compounds can be found in the list of possible additional stabilizers under the item 2.6 above.

Addition of the compounds of the formula (1) and, if desired, of further additives to the polymers can take place before or during shaping of the polymers, for example by mixing in pulverulent form or by addition to the melt or solution of the polymer or to a suitable coating formulation containing a polymeric binder.

Accordingly, the invention also provides the polymers stabilized by addition of at least one compound of the formula (1), which polymers can, if desired, also contain other additives. The polymers thus stabilized can be used in various forms, for example as fibres, foams, fibrous tapes, profiles, hollow articles, sheets, double-walled sheets or as binders for coatings, paints, adhesives and cements. Of particular interest is their use in coatings.

The novel UV absorbers are also suitable as light stabilizers in cosmetic preparations.

Accordingly, in a further aspect, the invention provides a cosmetic preparation comprising at least one compound of the general formula (1) and cosmetically compatible carriers or auxiliaries.

For cosmetic use, the light stabilizers according to the invention usually have an average particle size ranging from 0.02 to 2, preferably 0.05 to 1.5, and very particularly from 0.1 to 1.0 μ. The insoluble UV absorbers according to the invention can be brought to the desired particle size by customary methods, for example milling in a jet mill, ball mill, vibrating mill or hammer mill for example. Milling is preferably carried out in the presence of 0.1 to 30, preferably 0.5 to 15%, by weight, relative to the UV absorber, of a milling auxiliary, for example an alkylated vinylpyrrolidone polymer, a vinylpyrrolidone/vinyl acetate copolymer, an acylglutamate or, in particular, a phospholipid.

The cosmetic preparations can also contain, apart from the UV absorbers according to the invention, one or more further UV absorbers, for example oxanilides, triazoles, vinyl-containing amides or cinnamides.

Examples of suitable oxanilides are compounds of the formula

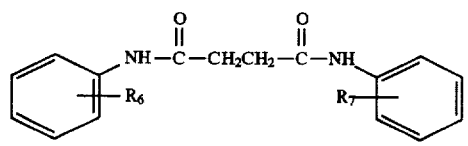

in which $R_6$ and $R_7$ are each independently of the other $C_1$–$C_{18}$alkyl or $C_1$–$C_{18}$alkoxy.

Preferred triazole compounds have the formula

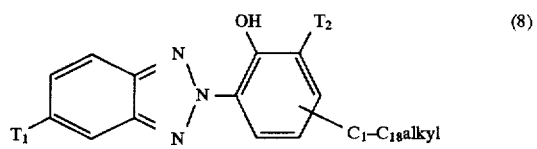

in which $T_1$ is $C_1$–$C_{18}$alkyl or, preferably, hydrogen; and $T_2$ is unsubstituted or phenyl-substituted $C_1$–$C_{18}$alkyl.

Another class of triazole compounds has the formula

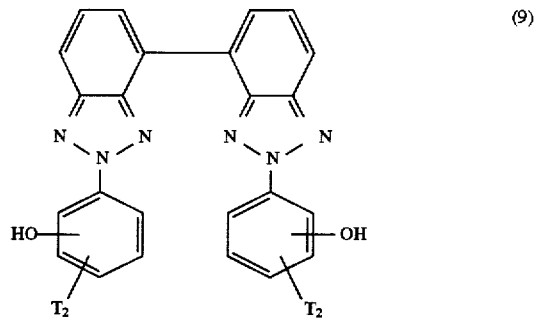

in which $T_2$ is as defined in formula (8).

Preferred vinyl-containing amides have the formula

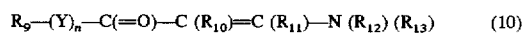

in which $R_9$ is $C_1$–$C_{18}$alkyl, preferably $C_1$–$C_5$alkyl, or phenyl where phenyl can be substituted by two or three substituents selected from hydroxyl, $C_1$–$C_{18}$alkyl or $C_1$–$C_{18}$alkoxy or a —C(=O)—OR$_8$ group, in which $R_8$ is $C_1$–$C_{18}$alkyl; $R_{10}$, $R_{11}$, $R_{12}$ and $R_{13}$ are each independently of one another hydrogen or $C_1$–$C_{18}$alkyl; Y is N or O; and n is 0 or 1.

Preferred cinnamic acid derivatives have the formula

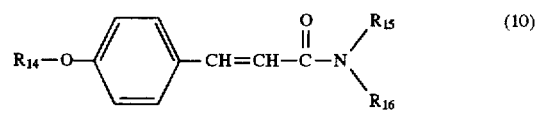

in which $R_{14}$ is hydroxyl or $C_1$–$C_4$alkoxy, preferably methoxy or ethoxy; $R_{15}$ is hydrogen or $C_1$–$C_4$alkyl, preferably methyl or ethyl; $R_{16}$ is —(CONH)$_n$phenyl, n is 0 or 1 and the phenyl ring can, if desired, be substituted by one, two or three substituents selected from OH, $C_1$–$C_{18}$alkyl or $C_1$–$C_{18}$alkoxy or a —C(=O)—OR$_8$ group where $R_8$ is as defined above.

The additional UV absorbers used in addition to the UV absorbers according to the invention are known, for example, from Cosmetics & Toiletries (107), 50ff (1992).

The cosmetic composition according to the invention comprises 0.1 to 15, preferably 0.5 to 10%, by weight, relative to the total weight of the composition, of a UV absorber or of a mixture of UV absorbers and a cosmetically acceptable auxiliary.

The cosmetic composition can be prepared by physical mixing of the UV absorber(s) with the auxiliary using customary methods, for example by simply combining the two materials with stirring.

The cosmetic preparation according to the invention can be formulated as a water-in-oil or oil-in-water emulsion, as an alcoholic oil-in-oil lotion, as a vesicular dispersion of an ionic or nonionic amphiphilic lipid, as a gel, a solid stick or as an aerosol formulation.

As a water-in-oil or oil-in-water emulsion, the cosmetically acceptable auxiliary preferably contains 5 to 50% of an oil phase, 5 to 20% of an emulsifier and 30 to 90% of water. The oil phase can contain any oil suitable for cosmetic formulations, for example one or more hydrocarbon oils, a wax, a natural oil, a silicone oil, a fatty acid ester or a fatty alcohol. Preferred mono- or polyhydric alcohols are ethanol, isopropanol, propylene glycol, hexylene glycol, glycerol and sorbitol.

The emulsifier used for the cosmetic formulations according to the invention can be any conventionally used emulsifier, for example one or more ethoxylated esters of natural derivatives, for example polyethoxylated esters of hydrogenated castor oil; or a silicone oil emulsifier, for example silicone polyol; an ethoxylated or unethoxylated fatty acid soap; an ethoxylated fatty alcohol; an ethoxylated or unethoxylated sorbitan ester; an ethoxylated fatty acid; or an ethoxylated glyceride.

The cosmetic formulation can also contain further components, for example emollients, emulsion stabilizers, skin moisturizers, skin-tanning accelerators, thickeners, for example xanthan, moisture-retaining agents, for example glycerol, preservatives, scents and dyes.

The cosmetic formulations according to the invention are distinguished by excellent protection of the human skin from the damaging effect of sunlight while simultaneously ensuring safe tanning of the skin. Moreover, when applied to the skin, the cosmetic preparations according to the invention are waterproof.

In the examples below, the percentages are by weight. The amounts of dyes and triazine compounds are based on the pure substance.

Example 1:2-(2-hydroxyphenyl)-4,6-bis(4-methoxyphenyl)-1,3,5-triazine 42 g of 4-methoxybenzamidine hydrochloride are first introduced into 100 ml of dimethylacetamide. 41.2 ml of a 30% sodium methoxide solution are added with stirring. After further addition of 33 g of methyl salicylate, the mixture is heated to 90° to 95° C. and stirred at this temperature for 20 hours. During the first three hours, about 62 ml of a mixture of methanol, dimethylacetamide and water distil off. 150 ml of methanol are added, the reaction mixture is cooled to 5° C., and the product is filtered off. After drying at 110° C., 30.6 g of a light yellow product of the formula

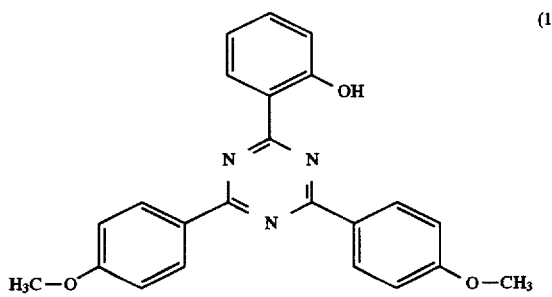

(101)

m.p. 205°–206° C. are obtained.

Examples 2 to 5: The compounds of the formulae (102)–(105) in Table 1 are prepared by the same method.

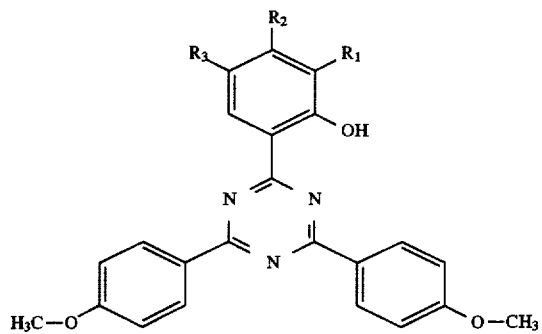

TABLE 1

| Example | Compound | R₁ | R₂ | R₃ | m. p. [°C.] |
|---|---|---|---|---|---|
| 2 | (102) | H | OH | H | 251-252 |
| 3 | (103) | CH₃ | H | H | 192-194 |
| 4 | (104) | H | CH₃ | H | 211-212 |
| 5 | (105) | H | H | Cl | 242-243 |

Example 6a:

37.2 g of 4-methoxybenzamidine hydrochloride are first introduced together with 100 ml of methanol. 36 g of a 30% sodium methoxide solution in methanol and 15.2 g of o-vanillin are then added. The mixture is stirred at 50° C. for 20 hours, then cooled, and 100 of water are added. After washing with a 1:1 mixture of methanol/water and drying at 100° C., 34 g of a light beige product of the formula

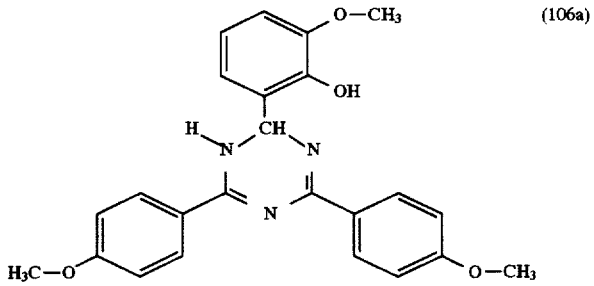

(106a)

are obtained.
Example 6b:

32 g of the dihydro product (106a) in 600 ml of acetone are first introduced together with 18.9 g of chloranil, and the resulting mixture is stirred at room temperature for 20 hours. The product is filtered off and dried to give 27.5 g of a light-coloured product of the formula

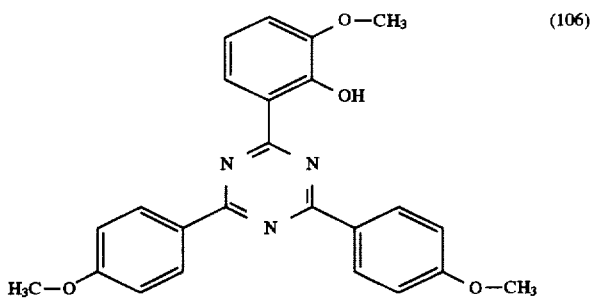

(106)

Yield: 86.4% of theory M.p.: 197°–198° C.

Example 7: 2-(2-hydroxy-4-methoxyphenyl)-4,6-bis(4-methoxyphenyl)-1,3,5-triazine The procedure described in Example 6 is repeated, except that 2-hydroxy-4-methoxybenzaldehyde is used instead of o-vanillin. This produces the corresponding dihydro product of the formula

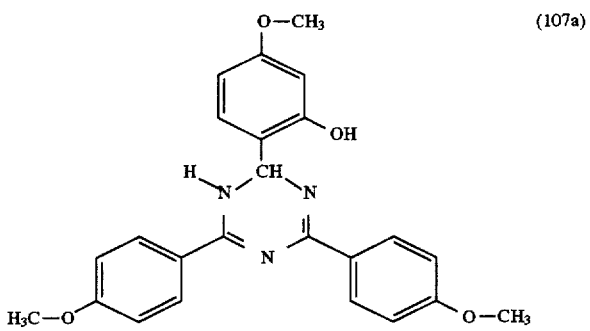

(107a)

in a yield of 41% of theory. Oxidation with chloranil gives the compound of the formula

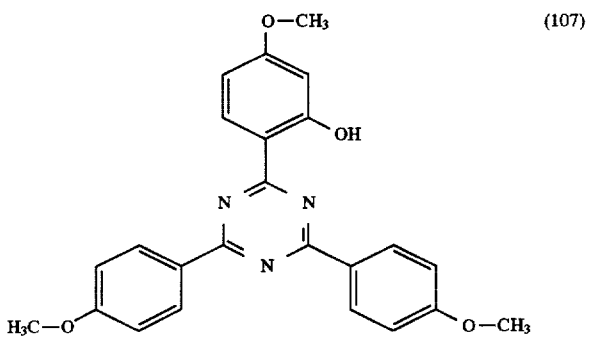

(107)

Yield: 77% of theory M.p.: 213°–214° C.

Example 8a: 2-chloro-4,6-bis(4-methoxyphenyl)-1,3,5-triazine

A Grignard solution of p-methoxyphenylmagnesium bromide (prepared from 12.2 g (0.05 mol) of magnesium and 93.5 g (0.5 mol) of p-bromoanisole in 130 ml of anhydrous THF) is added to a solution of 31.3 g (0.17 mol) of cyanuric chloride in 100 ml of THF over a period of 1.5 hours while maintaining the temperature in the range from 0° to 20° C. After addition is complete, the mixture is stirred at room temperature for 1.5 hours and then poured into 150 ml of 12% hydrogen chloride solution in an ice-bath. The beige suspension is filtered off, washed neutral with water and then washed with methanol. The crude product is recrystallized from 350 ml of toluene to give the compound of the formula

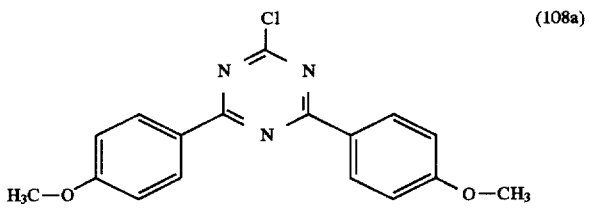

(108a)

Yield: 40 g (72% of theory) M.p.: 193°–195° C.

Example 8b: 2-(2,4-dihydroxyphenyl)-4,6-bis(4-methoxyphenyl)-1,3,5-triazine 10.3 g (0.077 mol) of aluminium chloride are added at 5° C. to a mixture of 23.0 g (0.07 mol) of 2-chloro-4,6-bis(4-methoxyphenyl)-1,3,5-triazine of the formula (108a) and 8.5 g (0.077 mol) of resorcinol in 150 ml of toluene. The temperature is allowed to rise to 20° C., and the mixture is then heated at 50° C. for 6 hours and refluxed for 24 hours. The cooled mixture is poured into 150 ml of 12% hydrogen chloride solution, the crude product is filtered off, washed neutral with water and then washed with methanol and dried to give a dark yellow product of the formula

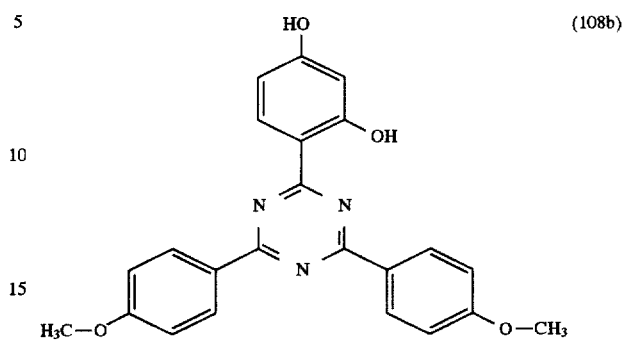

(108b)

Yield: 18.8 g (67% of theory) M.p.: 195°–198° C.

Example 9: 2-(2-hydroxy-4-hexyloxyphenyl)-4,6-bis(4-methoxyphenyl)-1,3,5-triazine 15.2 g (0.038 mol) of 2-(2,4-dihydroxyphenyl)-4,6-bis(4-methoxyphenyl)-1,3,5-triazine of the formula (108b), 5.2 g of potassium carbonate and 50 mg of potassium iodide are heated in 100 ml of 2-ethoxyethanol at 110° C. for 45 minutes, followed by dropwise addition of 6.9 g (0.042 mol) of 1-bromohexane over a period of 15 minutes. The mixture is stirred at 110° C. for 12 hours, cooled to 0° C. and filtered. The solid material is washed neutral with water and then washed with methanol and dried. After recrystallization from 2-ethoxyethanol, the pure light yellow product of the formula

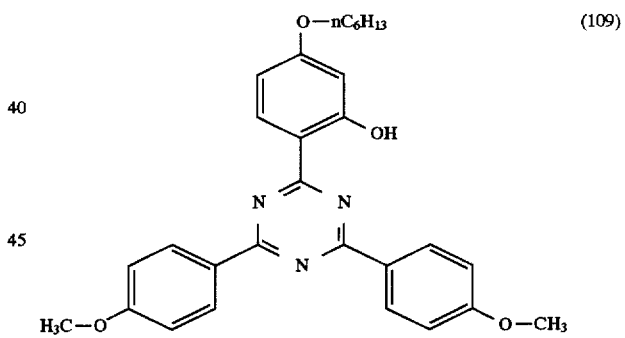

(109)

is obtained. Yield: 4.8 g (26% of theory) M.p.: 123°–125° C.

Example 10: 2-(2-hydroxy-4-hexyloxyphenyl)-4,6-bis(3-methoxyphenyl)-1,3,5-triazine 10 g (0.025 mol) of 2-(2,4-dihydroxyphenyl)-4,6-bis(3-methoxyphenyl)-1,3,5-triazine (prepared by the method of Example 8, starting with 3-bromoanisole), 3.8 g of potassium carbonate and 30 mg of potassium iodide are heated in 25 ml of 2-ethoxyethanol at 110° C. for one hour, followed by dropwise addition of 6.7 g (0.041 mol) of 1-bromohexane and stirring at 110° C. for another 32 hours. After cooling, the mixture is filtered, the solid material is washed neutral with water and then washed with methanol and dried. The crude product is purified by column chromatography (250 g of $SiO_2$ 35–70 μm; eluent 1:1 toluene/petroleum ether). This gives the compound of the formula

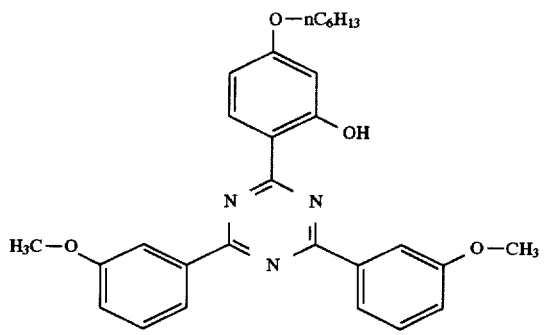

(110)

Yield: 3.4 g (28% of theory) M.p.: 127°–128° C.

Example 11:

4.9 g (10.86 mmol) of benzamidine hydrochloride (38% in methanol) and then a solution of 1.95 g (10.86 mmol) of sodium methoxide (30% in methanol) are added to a suspension of 2.83 g (10 mmol) of 7-methoxy-2-(4-methoxyphenyl)-4H-1,3-benzoxazin-4-one in 48 ml of methanol. The mixture is heated to boiling and diluted with 38 ml of methanol. After refluxing (30 minutes), the precipitate is filtered off with suction while hot and washed twice with 10 ml of methanol each time. Recrystallization from chloroform/petroleum ether gives 3.74 g (97% of theory) of the product of the formula

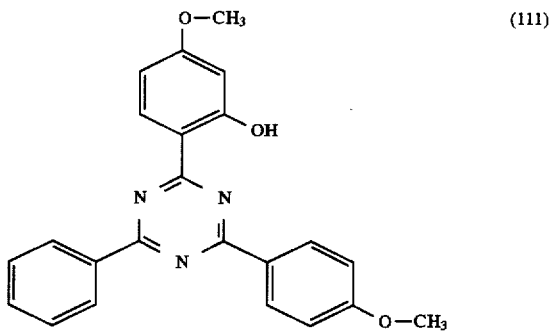

(111)

M.p.: 171°–172° C. UV spectrum (2.25·10$^{-5}$ mol in chloroform) $\lambda_{max}/\epsilon_{max}$=297/34920 325/shoulder Example 12:2-{4,6-bis-[4-(2-ethylhexyloxy)-phenyl]-s-triazin-2-yl}-5-(2-ethylhexyloxy)-phenol a) A 1 l sulfonating flask equipped with stirrer, cooler, dropping funnel and internal thermometer is charged with 61.4 g (0.5 mol) of 4-hydroxybenzonitrile in 500 ml of methylcellosolve. After heating the batch to 80° C., 73.3 g of 30% NaOH (0.55 mol) are slowly run in with vigorous stirring. Stirring is continued for 15 minutes before adding 116.8 g (0.575 mol) of 3-bromomethylheptane dropwise over a period of 30 minutes. The reaction is continued at 100° C. for about 12 hours. The thin-layer chromatogram shows almost quantitative conversion. The solvent and excess bromide are removed in vacuo, and the residue (oil) is taken up in 500 ml of toluene. The resulting mixture is extracted three times with water, the organic phase is dried over sodium sulfate and evaporated to dryness. High-vacuum distillation through a 10-cm Vigreux column (127°–132° C., 0.15 mmHg) gives 97.5 g (84% of theory) of 4-(2-ethylhexyloxy)benzonitrile as a coloured oil.

b) A 1.5 l plane ground-joint reactor equipped with stirrer, cooler, internal thermometer and gas inlet tube is charged with 208.7 g (0.9 mol) of 4-(2-ethylhexyloxy)benzonitrile and 39.8 g (1.22 mol) of methanol in 400 ml of dichloroethane. 85.4 g (2.37 mol) of hydrogen chloride gas are introduced over a period of 5 hours with vigorous stirring and ice cooling (0°–1° C.). After 24 hours of stirring at room temperature, the thin-layer chromatogram shows quantitative conversion to the imido ester. The solvent is removed in vacuo, and the yellow viscous residue is run into a thoroughly stirred solution of 34 g (2.0 mol) of ammonia in 800 ml of methanol over a period of 30 minutes with ice-cooling (0°–10° C.). Stirring at room temperature is continued for 1 hour and at 50°–60° C. for another 90 minutes. The batch is evaporated to dryness in vacuo, the greasy residue is then stirred in 800 ml of warm 8:2 toluene/ethanol, and the mixture is filtered through silica gel. This removes a large portion of the ammonium chloride formed. The filtrate is concentrated, and this purification is repeated two more times. This gives 205 g (80% of theory) of the amidinium salt (m.p. 172°–173° C.), which still contains small amounts of ammonium chloride.

c) In a 2.5 l sulfonating flask equipped with stirrer, cooler, internal thermometer and dropping funnel and pH electrode, 113.9 g (0.4 mol) of the amidinium salt obtained in b) are suspended in a mixture of 1000 ml of distilled water and 100 ml of acetone. 106.7 g of 30% sodium hydroxide solution (0.8 mol) are slowly added at 15°–20° C. over a period of 30 minutes. 45.6 g (0.42 mol) of ethyl chloroformate are then added dropwise over a period of one hour (internal temperature: 15°–20° C.). Over the course of the reaction, the pH drops from 13 (initial value) to 7.0–7.5, and a granular suspension is obtained. After adding 500 ml of 1,2-dichlorobenzene, the mixture is heated to 80° C. with stirring. The organic phase is separated off in a separatory funnel, transferred to a 1.5 l sulfonating flask (equipped with a Liebig condenser) and heated to 145°–175° C. (internal temperature) under a slight vacuum (about 800 mbar). The urethane formed in the ring-closure condensation is distilled off (duration about 90 minutes). The brown reaction mass is run into 600 ml of isopropanol at 60° C., the precipitate is filtered off with suction in the cold (5° C.) and washed with isopropanol, water and methanol. It is then dried in vacuo (100° C.). The product 4,6-bis[4-(2-ethylhexyloxy)phenyl]-s-triazin-2-ol exhibits a blue fluorescence and is shown by thin-layer chromatography to be uniform. The yield is 57 g (56% of theory; m.p. 168°–170° C.).

d) A 1.5 l sulfonating flask equipped with stirrer, cooler, internal thermometer, dropping funnel and gas outlet is charged with 55.6 g (0.11 mol) of 4,6-bis[4-(2-ethylhexyloxy)-phenyl]-s-triazin-2-ol in 300 ml of xylene to which 1 ml of dimethylformamide has been added. 17.0 g (0.14 mol) of thionyl chloride are added dropwise at an internal temperature of 75°–80° C. over a period of 15 minutes with vigorous stirring. After the evolution of gas subsides, the temperature is raised to 100° C. After 2 hours, the reaction is complete (checked by thin-layer chromatography). Excess thionyl chloride is distilled off from the reaction vessel under a slight vacuum, and the intermediate 2-chloro-4,6-bis[4-(2-ethylhexyloxy)-phenyl]-s-triazine is directly reacted further. 16.2 g (0.12 mol) of dry sublimed aluminium chloride is introduced at 50° C. (in about 1 minute), which raises the temperature to 65° C. The initially clear yellow solution turns into a red and then olive-coloured suspension. 13.3 g (0.12 mol) of resorcinol are added in portions at 50°–55° C. (over a period of about 10 minutes), and the mixture is then heated to 85° C. After 3 hours, the thin-layer chromatogram shows no more starting material. The mixture is cooled to 70° C., and the aluminium complex is hydrolysed by slow dropwise addition of 300 ml of 5% hydrochloric acid, during which the temperature should not exceed 80° C. The solvent (xylene) is removed by steam distillation, the greasy residue is stirred in 500 ml of hot toluene, and the resulting mixture is filtered through silica gel. The filtrate is digested with activated carbon and filtered again. The filtrate is dried with sodium sulfate, and the solvent is distilled off. For further purification, the brown viscous residue (69 g) is dissolved in 150 ml of 95:5 toluene/ethyl acetate, and the resulting solution is subjected to column chromatography (6 cm×60 cm silica gel 60). This gives 33.6 g (51% of theory) of 4-{4,6-bis[4-(2-ethylhexyloxy)phenyl]-s-triazin-2-yl}-1,3-dihydroxybenzene a yellow viscous oil.

e) A 1 l sulfonating flask equipped with stirrer, condenser, internal thermometer and dropping funnel is charged at 80° C. with 83.7 g (0.14 mol) of 4-{4,6-bis[4-(2-ethylhexyloxy)phenyl]-s-triazin-2-yl}-1,3- dihydroxybenzene together with 500 ml of methylcellosolve. 18.1 g of 30% sodium hydroxide solution (0.16 mol) are added, stirring is continued for 15 minutes, and a solution of 31.4 g (0.16 mol) of 3-bromomethylheptane and 30 ml of methylcellosolve is then added dropwise over a period of 30 minutes. After 24 hours of stirring at 110° C., alkyladon is complete (thin-layer chromatogram). The mixture is evaporated to dryness in vacuo, the residue is dissolved in 500 ml of toluene, the resulting solution is filtered, and the filtrate is extracted with water. The organic phase is dried over sodium sulfate and the solvent is distilled off to give 100.9 g of a red-brown oil. The crude product is dissolved in 200 ml of 97.5:2.5 toluene/ ethyl acetate and purified by chromatographing it through silica gel (10 cm×40 cm). This gives 79.4 g (80% of theory) of the compound of the formula at 80° C. in vacuo to give 125.5 g (54.4% of theory) of phenyl 2,4-dihydroxybenzoate (m.p. 135°–137° C.).

b) A 750 ml sulfonating flask equipped with stirrer, condenser, internal thermometer and dropping funnel is charged with 200 ml of absolute ethanol and 12.1 g (0.22 mol) of sodium ethoxide at room temperature. 59.9 g (0.21 mol) of amidinium hydrochloride (for preparation, see Example 12 b)) are introduced and stirring is continued for 30 minutes. The precipitated sodium chloride is then filtered off (silica gel). A solution of 23.0 g (0.1 mol) of phenyl 2,4-dihydroxybenzoate (prepared in Example 13 a)) in 100 ml of absolute ethanol is added at room temperature, the clear red-yellow solution is refluxed for 3 hours with stirring (78° C.). About 150 ml of ethanol is distilled off, and the same volume of ethylcellosolve is added. The batch is maintained under reflux overnight (90° C.). The reaction mixture is evaporated to dryness in vacuo, the residue is stirred twice with hot water, and the residue is dissolved in 500 ml of toluene. After filtration of the cloudy solution through silica gel, the filtrate is dried with sodium sulfate, and the solvent is distilled off in vacuo. The crude product (68.2 g) is dissolved in 120 ml of toluene and chromatographed over silica gel 60 (6 cm×60 cm) (eluent 95:5 toluene/ethyl acetate). 28.5 g (48% of theory) of 4-{4,6-bis [4-(2-ethylhexyloxy)phenyl]-s-triazin-2-yl}-1,3-dihydroxybenzene are isolated as a yellow viscous oil.

c) A 250 ml sulfonating flask equipped with stirrer, condenser, internal thermometer and dropping funnel is

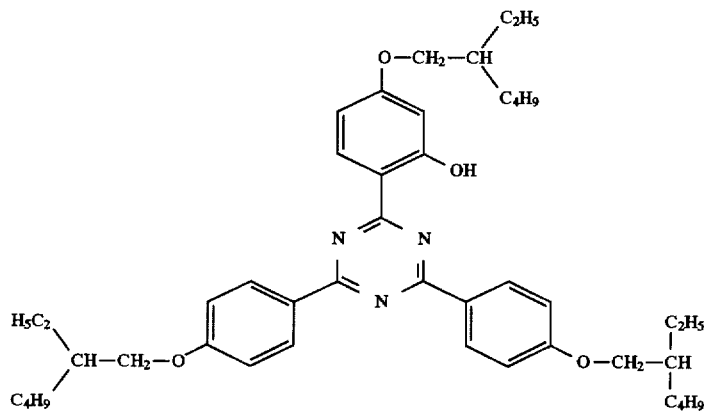

as a honey-like, red-brown resin.

Example 13: ethyl 4-{4,6-bis[4-(2-ethylhexyloxy)phenyl]-s-triazin-2-yl}-3-hydroxyphenoxy)acetate a) A 1.5 l sulfonating flask equipped with stirrer, condenser, dropping funnel and gas outlet is charged with 154.1 g (1.0 mol) of 2,4-dihydroxybenzoic acid, 141.2 g (1.5 mol) of phenol, 500 ml of toluene and 1 ml of dimethylformamide. 178.5 g (1.5 mol) of thionyl chloride are then added dropwise at an internal temperature of 100°–105° C. over a period of 2.5 hours. The reddish clear solution is then refluxed overnight (110°–115° C.). The toluene and the phenol are distilled off in vacuo, the highly viscous residue (271.5 g) is stirred in 300 ml of 7:3 toluene/cyclohexane, and the product is allowed to crystallize overnight. The precipitate is filtered off with suction while cold (10° C.) and washed with 3×50 ml of 7:3 toluene/cyclohexane. It is dried charged at 60° C. with 14.4 g (0.024 mol) of the compound prepared in b) together with 150 ml of absolute ethanol. 3.4 g of a 30% sodium hydroxide solution (0.025 mol) are added, stirring is continued for 15 minutes, and 4.8 g (0.028 mol) of ethyl bromoacetate are then added dropwise over a period of 10 minutes. After 24 hours of stirring under reflux, alkylation is complete (thin-layer chromatogram). The mixture is evaporated to dryness in vacuo, the residue is taken up in 250 ml of toluene and extracted twice with water. The organic phase is dried over sodium sulfate and the solvent is distilled off to give 17.1 g of a red-brown oil. The crude product is dissolved in 50 ml of toluene and is purified by chromatographing it over silica gel. This gives 9.0 g (55% of theory) of the compound of the formula

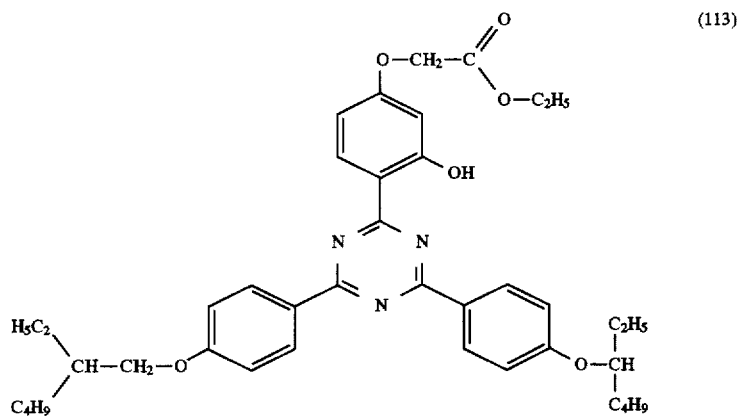

(113)

as an orange resin which crystallizes after a few days. (M.p. 93°–95° C.).

Example 14: 2-{4,6-bis[4-(2-ethylhexyloxy)phenyl]-s-triazin-2-yl}-5-(2-ethylhexyloxy)-phenol a) A 1 l sulfonating flask equipped with stirrer, condenser, dropping funnel and internal thermometer is charged with 86.5 g (0.5 mol) of 4-bromophenol in 500 ml of methylcellosolve. After the mixture is heated to 60° C., 70.0 g of 30% NaOH (0.53 mol) are slowly run in. Stirring is continued for 15 minutes before 116.8 g (0.575 mol) of 3-bromomethylheptane are added dropwise over a period of 45 minutes. The reaction is continued overnight at 100° C. The thin-layer chromatogram shows almost quantitative conversion. Solvent and excess bromide are removed in vacuo, and the residue (oil) is taken up in 600 ml of toluene. The resulting solution is extracted three times with water. The organic phase is dried over sodium sulfate and evaporated to dryness to give 119.3 g (84% of theory) of 4-(2-ethylhexyloxy)bromobenzene as a light yellow oil.

b) A 100 ml sulfonating flask equipped with stirrer, condenser, drying tube, dropping funnel and internal thermometer is charged under inert gas (dry nitrogen) with 3.65 g (0.15 mol) of magnesium turnings, and a few crystals of iodine are added as catalyst. 150 ml of anhydrous tetrahydrofuran are added, and a solution of 42.8 g (0.15 mol) of 4-(2-ethylhexyloxy)bromobenzene in 30 ml of tetrahydrofuran is added dropwise over a period of 45 minutes (room temperature). After slight heating on a water bath (40° C.), the Grignard reaction starts (cloudiness, exothermic reaction). The reaction mixture is stirred at 40° C. for one hour and then under reflux (66° C.) until the magnesium is almost completely dissolved (about 30 minutes). After cooling to room temperature, the Grignard solution is added dropwise at 0°–20° C. to a solution of 9.2 g (0.05 mol) of cyanuric chloride in 40 ml of tetrahydrofuran over a period of 60 minutes (350 ml sulfonating flask, stirrer, condenser, drying tube, dropping funnel, internal thermometer, inert gas). The mixture is stirred overnight under reflux (66° C.) and then evaporated to dryness. The residue is stirred in 100 ml of ice 2N hydrochloric acid and then extracted with 200 ml of toluene. The organic phase is shaken twice with 10% brine, dried over sodium sulfate and evaporated. The crude product (40.3 g, red oil) is still very impure (thin-layer chromatogram). For purification it is dissolved in 80 ml of 1:1 toluene/hexane and chromatographed over silica gel (5 cm×45 cm). 18.2 g (69.5%) of 2-chloro-4,6-bis[4-(2-ethylhexyloxy)phenyl]-s-triazine are isolated as a yellow resin.

c) Friedel-Crafts acylation is carried out as described in Example 12 d). The product 4-{4,6-bis[4-(2-ethylhexyloxy)phenyl]-s-triazin-2-yl}-1,3-dihydroxybenzene is obtained.

d) Alkylation is carried out as described in Example 12 e). The end product is the compound of the formula (112).

Examples 15 to 17:

Following the methods described in Examples 12 to 14 also provides the following compounds (Table 2):

TABLE 2

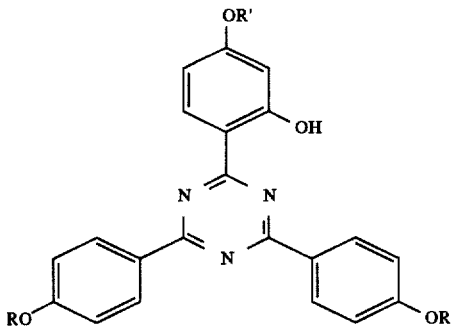

| Ex. | Compound of the formula | R | R' | M.p. [°C.] |
|---|---|---|---|---|
| 15 | (115) | n-dodecyl | $CH_2-CO_2C_2H_5$ | yellow oil |
| 16 | (116) | n-dodecyl | n-dodecyl | yellow oil |
| 17 | (117) | $-CH_2-HC\begin{smallmatrix}C_2H_5\\C_4H_9\end{smallmatrix}$ | H | 94–95 |

Application examples

Example 18:

8 10 g samples of a PES knitted fabric are dyed in an HT-dyeing machine, for example in a Labomat® from Mathis, Niederhasli, at a liquor ratio of 10:1. The liquors contain in each case 2 g/l of ammonium sulfate, 0.5 g/l of a dyeing assistant, for example ®Univadin 3-flex and the following dyes in the amounts given:

0.210% of the dye (1) C.I. DISPERSE YELLOW 42 0.087% of the dye (2) C.I. DISPERSE RED 302 0.080% of the dye (3) C.I. DISPERSE VIOLET 57 0.087% of the dye (4) C.I. DISPERSE BLUE 60.

While liquor (I) does not contain any further additives (stabilizers), an additional 0.6% of the compounds listed in Table 3 by their numbers is added to liquors (II)–(VIII).

The compounds had previously been milled to a particle size of 1–2μ together with 2 parts of a nonionic dispersant in a ball mill or in a high-speed stirrer.

The pieces of knitted fabric are dyed in the dispersed liquor in pressurized autoclaves. To this end, the dyeing liquor is entered at 50° C. and heated after 5 minutes to 130° C. at 3°/minute. This temperature is maintained for 45 minutes. The liquor is then cooled to 50° C., and the dyed material is thoroughly rinsed with deionized water and dried.

To determine the light fastness, the dyed fabric is exposed to light by the method of SAEJ 1885. The results are listed in Table 3.

TABLE 3

| Liquor | | Colour shift factor ΔE as determined by CieLab D 65/10 SAEJ 1885 488 kJ |
|---|---|---|
| (I) | none * | 6.3 |
| (II) | 0.6% of (103) | 2.8 |
| (III) | 0.6% of (106) | 2.4 |
| (IV) | 0.6% of (107) | 2.9 |
| (V) | 0.6% of (102) | 2.5 |
| (VI) | 0.6% of (104) | 2.4 |
| (VII) | 0.6% of (101) | 2.0 |
| (VIII) | 0.6% of (111) | 2.1 |

* mean value from 10 determinations

The results from Table 3 show that the fibre materials treated according to the invention have significantly improved light fastness properties compared with the corresponding untreated material.

Example 19: Application in PES printing

In order to print a PES knitted fabric, the printing pastes listed below are prepared. The individual components present in these pastes, i.e. stock thickener, dye, water and the UV absorbers of the formulae (101) (=paste 2) and (107) (paste 3), are mixed with one another. The compounds of the formulae (101) and (107) are present in these pastes as 30% sand millings. Printing paste 1 does not contain any active substance.

The printing pastes 1, 2 and 3 contain in each case the following individual components:

(a) 750 parts of a stock thickener comprising:
9 parts of starch ether
18 parts of sodium alginate,
3.75 parts of sodium dihydrogen phosphate and
2.48 parts of sodium chlorate.
The thickening composition is brought to a total water content of 750 parts.

(b) 7.4 parts of a dye mixture of
2.4 parts of the dye C.I. Disperse Yellow 42
2.0 parts of the dye C.I. Disperse Red 302
2.4 parts of the dye C.I. Disperse Violet 57
2.4 parts of the dye C.I. Disperse Blue 60

(c) UV absorbers:
Paste 1: none
Paste 2: 30 parts of the milling of the compound of the formula (101)
Paste 3: 30 parts of the milling of the compound of the formula (107).

Each of the 3 pastes is made up to 1000 parts with water. The pieces of precleaned knitted fabric are printed with these printing pastes on a commercially available printing table. The samples obtained are dried at 120° C. and steamed at 178° C. for 8 minutes and reduction-cleared with 2 ml/l NaOH (36° Bé) and 3 g/l sodium dithionite at 70° C. for 30 minutes. This is followed by a hot and cold rinse, centrifugation and drying at 120° C.

The prints are tested for light fastness by the method of DIN 75.202 and SAE J 1885.

The following results are obtained (Table 4):

TABLE 4

| | Light fastness properties | |
|---|---|---|
| | 4 periods DIN 75.202 | 600 KJ by SAE J1885 |
| Paste 1 | 1–2 | 1 |
| Paste 2 | 4 | 3–4 |
| Paste 3 | 3–4 | 3 |

(Ratings from 1–5 based on the grey scale).

The results from Table 4 show that the fibre materials treated according to the invention (paste 2 and paste 3) exhibit clearly improved light fastness properties compared with the corresponding untreated material (paste 1).

Example 20: Application for cosmetic light protection
Preparation of an o/w emulsion
Phase (A):
3 g of the compound of the formula (112) are dissolved in
10 g of sesame oil,
4 g of glyceryl stearate,
1 g of stearic acid,
0.5 g of cetyl alcohol and
0.2 g of polysorbate 20 are then added and fused with the rest.

Phase (B):
0.005 g of proplyparaben and
0.15 g of methylparaben are dissolved in
44 g of propylene glycol.
60 ml of water are then added, and the resulting mixture is heated to 70° C.
0.1 g of Carbomer 934 is emulsified therein.

Phase (A) is slowly added to phase (B) with vigorous introduction of mechanical energy. The volume is brought to 100 ml by addition of water.

After adding 3% of the UV absorber of the formula (112), the emulsion obtained has a sun protection factor (as defined by B. L. Diffey and J. Robson, J. Cosmet. Chem. 40, 127–133 (1989)) SPF of 17.

The sun protection factor can be changed by varying the UV absorber concentration. Table 5 below shows light protection factors for various concentrations of the UV absorber of the formula (112):

TABLE 5

| UV absorber Compound of the formula (112) [%] | Light protection factor according to Diffey and Robson |
|---|---|
| 0.5 | 2 |
| 1 | 5 |
| 1.5 | 10 |
| 2 | 13 |
| 3 | 17 |

Example 21: Application for cosmetic light protection:
0.5 g of the UV absorber of the formula (113) and 5.5 g of the phospholipid Phospholipon 90 or Phospholipon 90H are dissolved together in 109 ml of N-Methylpyrrolidone. 0.2 g of hexadecyltrimethylammoniumchloride is first dissolved in 190 ml of a 1:10 water/ethanol mixture, and the resulting mixture is added to the solution of UV absorber and phospholipid. The resulting mixture is added dropwise to 2 l of 0.03% aqueous NaCl solution, resulting in the formation of unilamellar vesicles. The vesicular suspension is concentrated to 100 ml by diafiltration, and the solvent is exchanged for aqueous 0.03% NaCl solution. 0.6 g of hydroxycellulose and 0.1 g of 2-bromo-2-nitropropane-1,3-thiol are then added. The vesicle diameters are (150±50) nm as determined by photon correlation spectroscopy. The formulation has a sun protection factor SPF of 3 as determined by the method of Diffey and Robson.

Example 22: Application for cosmetic light protection:

1.2 g of the UV absorber of the formula (117) and 6.1 g of the phospholipid Phospholipon 90 or Phospholipon 90H are dissolved together in 70 ml of N-Methylpyrrolidone. 0.33 g of hexadecyltrimethylammoniumchloride is first dissolved in 190 ml of a 1:10 water/ethanol mixture, and the resulting mixture is added to the solution of UV absorber and phospholipid. The resulting mixture is added dropwise to 2 l of 0.03% aqueous NaCl solution, resulting in the formation of unilamellar vesicles. The vesicular suspension is concentrated to 100 ml by diafiltration, and the solvent is exchanged for aqueous 0.03% NaCl solution. 0.6 g of hydroxycellulose and 0.1 g of bronopol are then added.

The vesicle diameters are (150±50) nm as determined by photon correlation spectroscopy.

The formulation has a sun protection factor SPF of 6 as determined by the method of Diffey and Robson.

Example 23: Application in organic polymers 10 g of polycarbonate powder (Lexan® 115) are dissolved in 50 g of methylene chloride at room temperature with stirring, which takes several hours. 0.2 g of UV absorber, which corresponds to an additional concentration of 2%, is added. These solutions are used to produce cast films 20 μm in thickness.

The films are exposed in an Atlas Weatherometer CI 65 at a black panel temperature of 63° C., an energy of radiation of 0.35 W/m² at 340 nm and a relative humidity of 60%. Discoloration of the samples is monitored at regular intervals by measuring the Yellowness Index (YI, ASTM method D 1925). Table 7 shows the exposure time up to a Yellowness Index of 7.

Exposure of the films is then continued until they become brittle, which is indicated by formation of cracks in the films. The exposure time until the films become brittle is also shown in Table 6.

TABLE 6

Exposure time (h) until a Yellowness Index (YI) of 7 is reached and until the films become brittle

| UV absorber of the formula | Exposure time (h) until | |
|---|---|---|
| | a YI of 7 | the films become brittle |
| none | 590 | 1375 |
| (111) | 2100 | 5000 |
| (101) | 1480 | 4980 |
| (110) | 1850 | 4020 |

Example 24: Application in organic polymers

Polycarbonate powder is mixed with 0.3% of UV absorber, and the mixture is granulated by processing in a twin-screw extruder (25 revolutions per minute) at a melt temperature of 275° C.

The granules are processed in an injection-moulding machine (240/300° C./75 bar) to give sheets of 67×43×2 mm. The sheets are exposed in an Atlas Weatherometer CI 65 as in Example 23. Table 7 shows the exposure time until a Yellowness Index (YI measured by ASTM D-1925) of 10 and 20 is reached.

TABLE 7

Exposure time (h) until reaching a Yellowness Index (YI) of 10 and 20

| UV absorber of the formula | Exposure time (h) | | |
|---|---|---|---|
| | YI at the beginning | until YI = 10 | until YI = 20 |
| none | 3.2 | 250 | 780 |
| 0.3% of (101) | 4.4 | 950 | 2700 |

What is claimed is:

1. A method of stabilizing organic polymers against damage by light, oxygen and heat, which comprises adding to said polymer an effective stabilizing amount of a compound of formula:

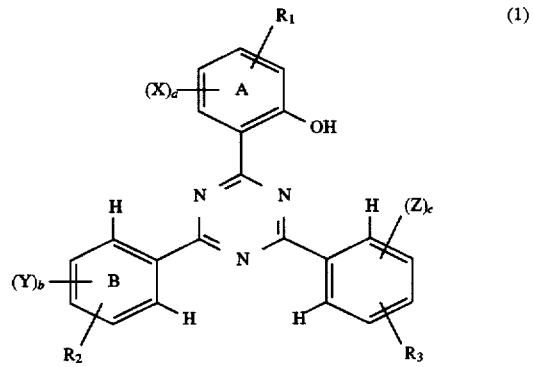

in which $R_1$ is hydroxyl, halogen, $C_1$-$C_{15}$alkyl, $C_1$-$C_{15}$alkoxy or a radical of the formula

$R_2$ and $R_3$ are each independently of the other hydrogen or $C_1$-$C_{15}$alkoxy; $R_4$ is $C_1$-$C_5$alkyl or $C_1$-$C_5$alkoxy-$C_1$-$C_5$alkyl; Q is an $C_1$-$C_4$alkylene radical; X, Y and Z are independently of one another halogen, hydroxyl, $C_1$-$C_{15}$alkyl or $C_1$-$C_{15}$alkoxy; a is an integer from 0 to 3; and b and c are each independently of the other an integer from 0 to 2; wherein the compound contains at least two $C_1$-$C_{15}$alkoxy radicals.

2. A stabilized organic polymer containing, as stabilizer for protection against light, oxygen and heat, at least one compound of the formula (1) according to claim 1.

3. A stabilized polymer according to claim 2, wherein the polymer is a binder for a coating.

4. A stabilized polymer according to claim 3, wherein the polymer additionally contains one or more further stabilizers and/or other additives.

5. A stabilized polymer according to claim 4, wherein the polymer additionally contains a light stabilizer from the class of sterically hindered amines and/or from the class of 2-(2'-hydroxyphenyl)benzotriazoles.

* * * * *